United States Patent [19]
Kramer Primus et al.

[11] Patent Number: 5,906,490
[45] Date of Patent: May 25, 1999

[54] DENTAL PRODUCT, SHADING KIT AND METHOD

[75] Inventors: Carolyn M. Kramer Primus, Sarasota, Fla.; Paul D. Hammesfahr, Wyoming, Del.

[73] Assignee: Ceramco Inc., Burlington, N.J.

[21] Appl. No.: 08/944,793

[22] Filed: Oct. 6, 1997

Related U.S. Application Data

[60] Continuation-in-part of application No. 08/456,151, May 31, 1995, Pat. No. 5,685,717, which is a division of application No. 08/257,411, Jun. 9, 1994, Pat. No. 5,482,732.

[51] Int. Cl.⁶ .................................................. A61C 13/08
[52] U.S. Cl. ........................................ 433/203.1; 427/2.29
[58] Field of Search ...................... 433/203.1; 427/2.29, 427/419.4, 140, 142, 379; 206/63.5

[56] References Cited

U.S. PATENT DOCUMENTS

| | | | |
|---|---|---|---|
| Re. 35,484 | 3/1997 | McLaughlin | 427/2.26 |
| 4,029,632 | 6/1977 | Gross et al. | 260/42.15 |
| 4,170,823 | 10/1979 | Gross et al. | 32/8 |
| 4,235,686 | 11/1980 | Dart et al. | 204/159.19 |
| 4,298,738 | 11/1981 | Lechtken et al. | 546/22 |
| 4,324,744 | 4/1982 | Lechtken et al. | 260/932 |
| 4,386,912 | 6/1983 | Nagase et al. | 433/228 |
| 4,420,306 | 12/1983 | Orlowski et al. | 433/228 |
| 4,490,115 | 12/1984 | Orlowski et al. | 433/199 |
| 4,525,256 | 6/1985 | Martin | 204/159.18 |
| 4,553,940 | 11/1985 | Koblitz et al. | 523/115 |
| 4,737,593 | 4/1988 | Ellrich et al. | 568/15 |
| 4,985,472 | 1/1991 | Aosai et al. | 522/64 |
| 5,057,018 | 10/1991 | Bowen | 433/228 |
| 5,094,619 | 3/1992 | McLaughlin | 433/203.1 |
| 5,104,319 | 4/1992 | Evans et al. | 433/202.1 |
| 5,106,304 | 4/1992 | Chronister | 433/228 |
| 5,125,970 | 6/1992 | Klepacki | 106/35 |
| 5,162,130 | 11/1992 | McLaughlin | 427/2 |
| 5,228,907 | 7/1993 | Eppinger et al. | 106/35 |
| 5,246,889 | 9/1993 | Kasuga et al. | 501/3 |
| 5,308,391 | 5/1994 | Komma et al. | 106/35 |
| 5,346,397 | 9/1994 | Braiman | 433/223 |
| 5,346,866 | 9/1994 | Komma et al. | 501/59 |
| 5,364,890 | 11/1994 | Sakuma et al. | 522/92 |
| 5,500,760 | 3/1996 | Varaprased et al. | 359/272 |
| 5,588,834 | 12/1996 | Rest et al. | 433/26 |
| 5,591,030 | 1/1997 | Thiel et al. | 433/212.1 |
| 5,618,763 | 4/1997 | Frank et al. | 501/5 |

FOREIGN PATENT DOCUMENTS

| | | |
|---|---|---|
| 58437/86 | 12/1986 | Australia . |
| 0173567 | 10/1986 | European Pat. Off. . |
| 0315186 | 5/1989 | European Pat. Off. . |
| 336417 | 10/1989 | European Pat. Off. . |
| 0381153 | 8/1990 | European Pat. Off. . |
| 0478937 | 4/1992 | European Pat. Off. . |
| 0544145 | 6/1993 | European Pat. Off. . |
| 0630639 | 12/1994 | European Pat. Off. . |
| 0686378 | 12/1995 | European Pat. Off. . |
| 0695726 | 2/1996 | European Pat. Off. . |
| 4207180 | 9/1992 | Germany . |
| 4400073 | 7/1996 | Germany . |

*Primary Examiner*—John J. Wilson
*Attorney, Agent, or Firm*—Dale R. Lovercheck; James B. Bieber

[57] ABSTRACT

The invention provides a kit and method for the preparation of dental products. First, second and third materials are provided in labeled containers. Preferably the first, second and third materials are pastes or powders. The first material has a lightness value ($L_1$) when formed into a least opaque layer. The second material has a lightness value ($L_2$) when formed into a less opaque layer. The third material has a lightness value ($L_3$) when formed into a most opaque layer. The third lightness value is greater than the second lightness value, which is greater than the first lightness value. The lightness value differences between the third lightness value ($L_3$) and the first lightness value ($L_1$) are less than 10 CIE $L*a*b$ units.

26 Claims, No Drawings

DENTAL PRODUCT, SHADING KIT AND METHOD

This is a continuation-in-part of U.S. Ser. No. 08/456,151 filed May 31, 1995, now U.S. Pat. No. 5,685,717, incorporated herein by reference in its entirety, which is a division of U.S. Ser. No. 08/257,411, filed Jun. 9, 1994, now U.S. Pat. No. 5,482,732 incorporated herein by reference in its entirety.

The invention relates to a color-correlation kit and method for shading dental products. The dental product color-correlation method of the invention provides dental restorations which match a shade guide. By using a dental color-correlation kit the method of the invention provides dental products such as restorations having substantially constant lightness value, hue and/or chroma, from opaque to translucent composite.

The kits and methods of the invention are useful for making improved dental filling material, artificial teeth, crowns and bridges, such as temporary and permanent crowns and bridges. Prior art preparation of temporary and permanent crowns and bridges is discussed in the Dentist Desk Reference:

Materials, Instruments and Equipment; First Edition, American Dental Association, Copyright 1981, pages 131–133, incorporated herein by reference in its entirety.

Metal based composite dental restorations such as crowns and bridges comprise a metal framework called a "coping", which is covered by several layers of composite to simulate the appearance of natural teeth. The composite is applied in a plurality of layers, the first layer applied over the coping is called the "opaque composite layer", the purpose of which is to hide the metal framework. The second layer applied over the first layer is called the "body composite layer". The body composite layer exhibits translucence to a degree similar to that of the dentine layer of natural dentition. In addition, a second layer of "opacious body or dentin" composite is used in conjunction with the body material. The opacious body material is more opaque than body composite layer and is preferably used under the body composite or in place of the body material where the restoration is very thin. Preferably an incisal material layer is positioned over the body material layer. The incisal material layer has a translucency approximately equal to the translucency of the enamel layer of natural dentition. The outer surface is either covered with a very thin transparent layer or polished to a high gloss.

Color is imparted to a metal-based composite dental restoration by coloring the opaque and body composite layers. It is an objective in the production of dental restorations to make the restoration resemble as closely as possible the patient's natural teeth.

Recently, all-ceramic or fiber reinforced composite dental restorations have been introduced commercially. These restorations replace the metal coping with a ceramic or composite base, and because the metal base is eliminated, they can be made to more closely resemble natural dentition. But even with an metal-free restoration, there is obviously still a need to match the color of the patient's natural teeth. One way to color an all-ceramic or all composite restoration is to color the base by any of several techniques (e.g., the color may be incorporated in the base material itself, or the base may be stained with a ceramic or organic stain). The body composite, an incisal layer and a glaze may be cured, over the ceramic or composite base, as is the case with metal-based restorations.

Whether or not the composite restoration has a metal base, its apparent color is influenced by the color of the body composite layer and by the color of the layer just beneath the body composite. The incisal composite and glaze layers contribute little, if anything, to the perceived color of the restoration because they are quite translucent or transparent, and are, at most, only slightly colored. Since natural teeth have translucent layers, i.e., enamel and dentine, the restoration must have translucent layers on its surface to match as closely as possible the appearance of natural teeth. However, the translucency of the body composite layer complicates the task of matching the color of natural teeth. The thickness of the body composite varies from a rather thick layer in the middle to a thin layer at the gingival or incisal ends of the restoration. Thus, it is normal for the body composite layer thickness to vary from about ¼ to 1½ millimeters. Because of this variation in thickness, light penetrates the body composite layer to different depths before it is reflected back to the observer, and unless the layer just beneath is exactly the same color as the body composite, the apparent color of the restoration will vary over its surface with the thickness of the body composite.

Thus, the visually discerned color of an opaque object is determined by the amount of visible illuminating light reflected (from the surface of the object) to the observer. The perceived color of a composite dental restoration is mainly the result of the diffuse reflectance from the translucent body composite layer covering an underlying more opaque layer. Perceived color is thus a combination of the scattered and reflected color of the translucent layer plus the color reflected from the underlying layer. When the translucent layer varies in thickness, the amount of color contribution from the underlying layer will vary inversely with the thickness of the translucent layer. Therefore, unless the translucent layer and the underlying layer are closely related in color, the perceived color of the restoration will be dependent upon the thickness of the body material layer.

Accordingly, it is clear that it is desirable to provide composite dental restorations in which the body composite matches the color of the layer beneath. Heretofore, however, there has been no commercial dental composite restoration kits in which the body composite material, when cured, matched exactly the hue, chroma and lightness of the composite material of the layer just beneath. The resulting prior art restorations do not match the hue, chroma or value of the corresponding shade guide component. In order to compensate for this, the dental technician has often had to modify the color of the opaque and body composite or apply composite stains to different portions of the restoration to prevent the perceived color from varying to an undesirable degree from a preselected color of a shade guide. This was not only a time consuming task, but also the results were quite dependent upon the skill of the technician.

According to the invention, composite is produced having a predetermined hue, chroma and lightness to match the hue, chroma and lightness of an underlying, more opaque, layer. Preferably, an observer cannot visually discern any difference in hue, chroma and lightness in a composite including a layer of the translucent composite overlying the underlying layer, even though the translucent composite layer varies in thickness.

It is an object of the invention to provide a kit for the preparation of composite dental restorations having a layer of at least one translucent composite overlying a more opaque composite layer. The kit includes at least one labeled container of colored translucent paste and at least one labeled container of composite for the more opaque layer, and when the translucent paste and composite material for the more opaque layer are cured, the colors of the translucent composite and the more opaque composite layer match spectrophotometrically such that the two colors have less than 5 degrees difference in CIE hue angle.

It is an object of the invention to provide a method for making crowns and bridges having a translucent layer over an opaque layer, using a set of composites having a translucent paste having a translucent hue when formed into the translucent layer, and an opaque paste having an opaque hue when formed into the opaque layer, wherein the translucent hue is within 5 degrees of CIE psychometric hue angle of the opaque hue. In the dental restoration of the invention, the color-matched layers are both uniform and match each other.

"CIE L*a*b* units" as used herein refers to CIE L*a*b* units according to the 1976 standard.

"Composite", as used herein and in the dental restoration arts, refers to resin materials containing an inorganic or organic filler. Composite is used to cover the base or coping in a restoration such as a crown or bridge. An important function of the composite in a dental restoration is to provide the aesthetic appearance of natural dentition. "Composite", as used herein, includes the composite materials used in a dental restoration, as defined above, and also includes the base of a fiber reinforced dental restoration.

"Uniform color layer" as used herein means that the layer has substantially equal hue, chroma and lightness throughout and is free of composite stains or the like applied to only a portion of the surface of the layer to compensate for the failure of the two layers to match in color.

"Matching in color", as used herein, means that when a composite is made having the translucent composite layers overlying the more opaque layer, an observer cannot visually discern any non-uniformity in the substantially equal hue, chroma and lightness of the composite even though the thickness of the translucent composite layer may vary over the normal range of thicknesses for the body composite layer in a composite dental restoration (e.g., from about one-half millimeter to about one and one-half millimeters). When color is matched, the color, measured at infinite optical thicknesses of the translucent composite, is the same as the opaque composite.

BRIEF SUMMARY OF THE INVENTION

The invention provides a kit and method for the preparation of dental composites. First, second and third materials are provided in labeled containers.

Preferably the first, second and third materials are liquids, pastes or powders. The first material has a lightness value ($L_1$) when formed into a least opaque layer. The second material has a lightness value ($L_2$) when formed into a less opaque layer. The third material has a lightness value ($L_3$) when formed into a most opaque layer. The third lightness value is greater than the second lightness value, which is greater than the first lightness value. The lightness value differences between the third lightness value ($L_3$) and the first lightness value ($L_1$) are less than 10 CIE L*a*b units. Preferably, the first material has a first hue ($H_1$) when formed into the least opaque layer, the second material has a second hue ($H_2$) when formed into the less opaque layer, and the third material has a third hue ($H_3$) when formed into the most opaque layer. Preferably the first hue ($H_1$) and the second hue ($H_2$) are within 5 degrees of the CIE psychometric hue angle of the third hue ($H_3$).

DETAILED DESCRIPTION OF THE INVENTION

The invention provides a kit for the preparation of composite dental restorations. In accordance with a preferred embodiment of the invention a kit for dental composite is provided for making crowns and bridges having a translucent layer over an intermediate layer over an opaque layer. The kit includes a first set of pastes having a first, a second and a third paste. Preferably the first paste is formed from a first powder, the second paste is formed from a second powder and the third paste is formed from a third powder, for example by mixing each powder with a polymerizable liquid. Preferably the kit includes a second set of pastes having a first, a second and a third paste. The pastes may be formed for example by mixing.

The first paste has a first opacity ($O_1$), a first hue ($H_1$), first chroma ($C_1$) and first lightness value ($L_1$) when formed into the translucent layer. The second paste has a second opacity ($O_2$), a second hue ($H_2$), second chroma ($C_2$) and second lightness value ($L_2$) when formed into the intermediate layer. The third paste has a third opacity ($O_3$) a third hue ($H_3$), third chroma ($C_3$) and third lightness value ($L_3$) when formed into the opaque layer. The third opacity ($O_3$) is greater than the second opacity ($O_2$) which is greater than the first opacity ($O_1$). The layers are hardened for example by curing.

Preferably for each set of pastes the third lightness value ($L_3$) is greater than the second lightness value ($L_2$) and the second lightness value ($L_2$) is greater than the first lightness value ($L_1$). The lightness value differences between the third lightness value ($L_3$) and the first lightness value ($L_1$) is preferably less than 10 CIE L*a*b* units and more preferably less than 5 CIE L*a*b* units. Each of the first hue (H1) and the second hue ($H_2$) are less than 2 degrees of the CIE psychometric hue angle of the third hue ($H_3$).

In accordance with a preferred embodiment of the invention is provided a system of dental composite color matching by measuring reflectance of visible light from the outer surface of a comparative dental composite article at a plurality of wavelengths. A translucent paste is formed into a dental composite layer having an outer surface having a percent reflectance for each of a plurality of visible light wavelengths. At each wavelength the translucent layer percent reflectance is different from the article percent reflectance by a substantially constant percentage.

The invention provides a shading method with a color-correlation scheme to make coordinated shades of composites of varied translucency. Such composites are combined to make a dental restoration corresponding to one dental shade reference article. In accordance with the invention is provided greater fidelity in color between the materials to be sequentially applied to form dental composite products.

In accordance with a preferred embodiment of the invention dental technicians use at least two, and often three composite pastes to create a crown or bridge. An opaque composite paste is useful to hide a metal understructure. Dentin and opacious dentin composites are cured on top of the opaque composites to create the tooth anatomy. These latter composites are translucent. After polymerization, the tooth must visually match the shade guide tab designated in a dentist's prescription.

Prior art color-coordination has been limited to matching the chroma and lightness of porcelain. Color coordinates of translucent materials are dependent on the thickness of the sample unless the samples are thicker than the "infinite optical thickness". In the method and kit of the present invention all three color coordinates are used and the colors are matched with samples based on the intrinsic color or the color at infinite optical thickness.

In accordance with the invention to correlate the shades of the translucent composites, shaded composites are made of three transparencies. The infinite optical thickness of the most transparent composite is separately determined by making cured samples. The color coordinates and the reflectivity of the sample for visible light transmitted to the sample at each of several individual wavelengths (preferably at ten or more wavelengths between 400 and 700 mm) is measured with a Datacolor spectrophotometer. Preferably these wavelengths are uniformly distributed over the range of visible wavelengths. Measurements are made over black and over white backgrounds. From these measurements, the intrinsic color coordinates are determined. These coordinates approximate the color at the infinite optical thickness. That is, at this thickness and thicker, the color coordinates and the reflectivity of the samples change very little, no matter whether the background is white or black.

Next, pigments are added to one of the translucent composite pastes. The concentrations of pigments in the samples of composite pastes are adjusted visually (or spectrophotometrically) to match a shade guide tab. These samples are made of approximately the same thickness as the shade guide tab. After the visual match (or spectrophotometric percent reflective match at a plurality of wavelengths) of one translucent composite is obtained, the more opaque or less opaque composites are pigmented until their intrinsic color coordinates match those of the original composite.

From the color coordinates, and calibration data for the pigments, formulas are made that have the color coordinates desired. Such a system predicts an opaque and opacious dentin composites' chroma. The principles underlying the utilization of CIE color coordinates and their calculation from the spectral response of a given color are known to those skilled in the art of color analysis. For instance, see Billmeyer and Saltzman, PRINCIPLES OF COLOR TECHNOLOGY, Second Edition, John Wiley & Sons, 1981, especially pages 44–46, 80–83, and 174, and Judd and Wyszecki, COLOR IN BUSINESS, SCIENCE AND INDUSTRY, Third Edition, John Wiley & Sons, 1975, especially pages 139–169, for discussions of the methods used to calculate CIE color coordinates. Tables are available that give the products of the CIE standard observer functions and the spectral power for various CIE illuminants (e.g., daylight, incandescent, and fluorescent) for each wavelength. These tables are used to calculate the tristimulus values for standard daylight, incandescent, and fluorescent light sources for the sample under evaluation.

These trios of composites are prepared as described above and compared to prior art sold as Artglass Belleglass pastes. Values of lightness (L*), hue (h*) and chroma (C*) and the differences therein for dentin, opacious dentin and opaque composite layers are for composite formed from a system of dental composite pastes of the present invention.

Hue is the angle measured from the horizontal each point creates, by graphing the color coordinates a* and b* and connecting this point to the origin of the graph of b* (yellowness) verses a* (redness), and is found mathematically from equation 1. Chroma is the distance of each point from the origin, and is found mathematically from equation 2. Mathematically hue and chroma are expressed as:

$$\text{Hue} = \tan^{-1}(b^*/a^*) \quad (1)$$

$$\text{Chroma} = \sqrt{(a^{*2} + b^{*2})} \quad (2)$$

Consistency for hue, chroma and lightness value is provided in composites made in accordance with the invention.

Thus, the invention provides prematched shades for use in making composites products having consistent hue, chroma and lightness values.

The invention provides color matching sets of composite pastes, one paste being the material for a translucent composite and another paste being the material for a composite having a lesser degree of translucency than the first paste, such that, when the composites are cured, the composites match in color. The products provided by the invention may be in the form of paste.

The lightness values of the composite layers formed from paste in accordance with the invention decrease from a layer formed from a most opaque paste to a layer formed from a less opaque paste to a layer formed from a least opaque paste. The change in lightness value is substantially monotonic.

Materials for kits and methods in accordance with the invention preferably include a polymerization initiator. Polymerization of a polymerizable material, such as monomer, for kits, systems and methods of the invention is preferably initiated by light, heat or mixing of components. Materials for use in accordance with the invention preferably include a polymerizable monomer. Polymerization initiators and polymerizable monomers useful in materials for kits and methods in accordance with the invention are disclosed in DENTSPLY's U.S. Pat. Nos. 4,698,373; 4,711,913; 4,814,423; and 4,863,977 each incorporated herein by reference in its entirety, and particularly for the disclosures therein of polymerization initiators and polymerizable materials including monomers. Exemplary polymerizable material for use in accordance with the invention includes polymerizable acrylates such as alkyl substituted acrylates. Preferably pastes and powders for use in accordance with the invention include pigment(s) and/or filler, for example 10, 20, 40, 50 or more percent by weight of organic and/or inorganic filler particles.

Exemplary polymerizable material for use in accordance with the invention includes one or more polymerization initiators, such as two component self-curing initiators, heat cured initiators and/or photoinitiator(s) for example camphorquinone.

Shelf-stable separation-resistant polymerizable compositions for making a polymeric dental products are provided. Preferably, the separation-resistant polymerizable composition includes inorganic and/or organic particulate material such as polymer, polymerizable material and a polymerization initiator system adapted to initiate polymerization of the polymerizable material. The polymerizable composition preferably has a viscosity of from about 5,000 to about 1,000,000 cps at 25° C.

Preferably polymerizable compositions, in accordance with the invention, are photopolymerizable, heat curable and/or self curing compositions which are separation resistant. The invention provides photopolymerizable compositions adapted for use as polymeric compositions in fabrication of crowns and bridges.

Preferably a separation-resistant polymerizable composition has a viscosity of from about 5,000 to about 1,000,000 cps (at 25° C.). More preferably a VLC separation-resistant composition has a viscosity of from about 60,000 to about 900,000 cps (at 25° C.). In accordance with a preferred embodiment of the invention, the photopolymerizable composition includes particles of polymer, a polymerizable methacrylate or acrylate resin composition with a Brookfield viscosity from about 1500 to 400,000 cps (at 25° C.) and a photoinitiator system. The photopolymerizable compositions have a viscosity of from about 5,000 to about 1,000,000 cps (at 25° C.)

Preferably, a particulate polymer filler and/or inorganic filler is added to a polymerizable liquid or semi-solid material to form a separation resistant composition having a viscosity between about 5,000 to about 1,000,000 cps. The particulate polymer preferably includes particles of thermoplastic and/or thermoset polymers, such as polyolefins (e.g., polyethylene, polypropylene, etc.), polyacrylates, poly methacrylates (or copolymers of poly(meth)acrylates), or nylon. Preferably the polymer used in this composition is cross-linked and particulate, such as particulate copolymers of methacrylate or acrylate compounds. Preferably the particulate polymer is a blend of a cross-linked polymer of methyl methacrylate and a dimethacrylate, such as, ethylene glycol dimethacrylate, and a homopolymer of methyl methacrylate. The cross-linked, particulate copolymer utilized in a preferred separation-resistant composition is poly (methyl methacrylate-co-ethylene glycol dimethacrylate) formed from 90 to 99.95% by weight methyl methacrylate and from 0.05 to 10% by weight ethylene glycol dimethacrylate.

More preferably the cross-linked, particulate copolymer is formed from 99 to 99.9% by weight methyl methacrylate and from 0.1 to 1% by weight ethylene glycol dimethacrylate.

Particulate polymer may be included in the polymerizable composition of the invention. In a preferred embodiment of the invention particulate polymer is from about 2 to about 60% by weight of the overall composition, more preferably is 10 to 50% by weight most preferably is 20 to 40% by weight. Preferably particle size range of the particulate polymer utilized in the present invention is about 2 to about 200 microns. More preferably the particle size range of the polymer is about 10 to 150 microns and most preferably the particle size range of the polymer is about 20 to 100 microns. As the average particle size of the polymer shifts towards the high end of this range (about 150 to 200 microns), the polymer content of the polymerizable composition is increased (approaching 55–60% by weight) to produce a polymerizable composition with a viscosity of about 5000–1,000,000 cps at 25° C.

Preferably the polymerizable material of the composition of the invention comprises an ethylenically unsaturated, polymerizable material, such as methacrylate or acrylates. Murphy et al U.S. Pat. No. 4,844,144 discloses suitable polymerizable material. Preferably the polymerizable material is comprised of polymerizable urethane methacrylate or acrylates and esters of acrylic and methacrylic acids. Preferably the polymerizable material comprises a blend of urethane (meth) acrylates and has a density of about 1.10 to about 1.35 grams per milliliter (g/ml) at 25° C. for use with particulate polymers preferably of poly methylmethacrylate and/ or copolymers thereof. Preferably the polymerizable blend has a density of at least 1.12 g/ml at 25° C., and more preferably the polymerizable material has a density of at least 1.15 g/mL (at 25° C.). The viscosity of the polymerizable material is preferably from about 4,000 to about 300,000 cps (at 25° C.), and more preferably the viscosity of the polymerizable material is from about 10,000 to about 200,000 cps (at 25° C.).

Preferably the polymerization initiator system content of the polymerizable composition is 0.2 to 7.5% by weight, or more preferably is 0.5 to 5% by weight, or even more preferably is 0.7 to 2.0% by weight, and is most preferably about 1.0% by weight.

Preferably the difference in hue between a most opaque layer and least opaque layer is less than 2, and most preferably less than 1 degree.

The invention is now described by reference to a specific examples:

EXAMPLE 1

A paste material for use in accordance with the invention is made as set forth in the following Examples:

33.3 grams of the monomeric reaction product of 2 moles of hydroxyethyl(meth)acrylate and 1 mole of 2,4-trimethylhexamethylene diisocyanate, 9.18 grams of silanized glass particles, 19.16 grams of pyrogenic silica, 0.41 grams of tert-butyl-perisononanoate, 0.4 grams of benzopinacol, 0.15 grams of 2,4-dihydroxybenzophenone and 37.4 grams of acrylate polymer particles are mixed to form a paste. Three portions of paste are separately blended with pigments and placed into three labeled containers. The first portion of material in the first labeled container is blended with pigments to provide a material to having a first capacity ($O_1$) and a first lightness value ($L_1$) when formed into a least opaque layer. The second portion of material in the second labeled container is blended with pigments to provide a material to having a second capacity ($O_2$) and a second lightness value ($L_2$) when formed into a less opaque layer. The third portion of material in the third labeled container is blended with pigments to provide a material to having a third capacity ($O_3$) and a third lightness value ($L_3$) when formed into the most opaque layer. A portion of the first material, second material and third material are formed by brushing and patting into least opaque, more opaque and most opaque layers, each having a thickness less than 1.5 mm. The third opacity ($O_3$) is greater than the second opacity ($O_2$). The second opacity ($O_2$) is greater than the first opacity ($O_1$). The third lightness value ($L_3$) is greater than the second lightness value ($L_2$). The second lightness value ($L_2$) is greater than the first lightness value ($L_1$). The third material is formed into the most opaque layer on a ceramic substrate (alternatively a metal or fiber reinforced substrate may be used) and heat cured. The second material is formed into the less opaque layer on the most opaque layer and heat cured. The first material is formed into the least opaque layer on the less opaque layer and heat cured to form a crown and bridge.

EXAMPLE 2

An opaque paste is made by stirring 7.1 grams of titanium dioxide silaned, 5.8 grams of zirconium dioxide silaned, 42.9 grams of urethane dimethacrylate, 16 grams of triethylene dimethacrylate, 3.2 grams dipentaerythritol pentacrylate phosphoric acid ester (PENTA), 4.8 grams of tert-butyl peroxybenzoate(t-BPD)(Lucirin LR 8893 X) sold by Bayer, 1.9 grams of bicyclo(2.2.1)heptane-2,3-dione 1,1,7-trimethyl-(IS) (camphorquinone), 6.7 grams of fumed silica, 3.14 grams methacrylic acid, 6.74 grams dimethylamino-neopentylacrylate and 1.6 grams of pigments.

EXAMPLE 3

A least opaque (dentin) paste is made by stirring 11.1 grams of a mixture of 32 parts of triethylene glycol dimethacrylate also known as 2-propenoic acid, 2-methyl-1,2-ethanediyl-bis(oxy-2,1-ethanediyl)ester (TEGDMA), 32 parts ethoxylated bisphenol A dimethacrylate (EBPADMA), 32 parts cyclodi-2,2'-bis((4-[3-methacryloxy-2(1,12-dioxa-2,11-dioxo-3,10-diazadodecane)propoxyl]phenyl]) propane and four parts 2-propenoic acid, 2-methyl-(1-methylethylidene) bis (4,1-phanalyeneoxy-2,1-ethanediyl) ester (bis GMA), 11.1 grams of a mixture of 55 parts of cyclodi-2,2'-bis((4-[3-methacryloxy-2(1,12-dioxa-2,11- dioxo-3,10-diazadodecane)propoxyl]phenyl]) propane and 45 parts of 2-propenoic acid, 2-methyl-1,2-ethanediyl-bis (oxy-2,1-ethanediyl)ester (TEGDMA), 0.0058 grams of 2,6-Bis(1,1-dimethylethyl)-4-methylphenol (BHT), 0.046 grams of 1,4-diethyl-2,5-dihydroxy-dibenzoate, 0.23 grams of methanone, (2,hydroxy-methoxyphenyl)phenyl, 0.023 grams of bicyclo (2.2.1) heptane-2,3-dione 1,1,7-trimethyl-(IS) (CQ), 0.009 grams of ethyl-4-N,N-dimethylaminobenzoate (EDAB), 75.2 grams of barium fluoro alumina borosilicate (7726), and 2.32 grams of fumed silica.

Table 1 compares the lightness value, chroma and hue differences between opaque and dentin composite materials for ArtGlass, Belleglass, Lucipast with Example 2 (opaque) and Example 3 (dentin). Each opaque paste is coated onto a metal button, polymerized and then measured for lightness value (L*) chroma (C*) and hue (Opaque minus Dentin: CIE color coordinates). Each least opaque (dentin) paste is formed into a 3 mm thick button, polymerized and then measured for lightness value, chroma and hue.

TABLE 1

Variation in Intrinsic Colors between Opaque and Dentin Composite Materials

| Material | $\Theta L^*$ | $\Theta C^*$ | $\Theta hue(°)$ |
|---|---|---|---|
| ArtGlass | 13.5 | 0.3 | −4.1 |
| BelleGlass | 21.6 | 12.9 | −3.0 |
| Licupast | 16.4 | −0.7 | −4.0 |
| Examples 2 and 3 (Opaque and Dentin Composite Materials) | less than 2.5 | less than 5 | less than 1 |

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A method of making a polymeric dental product, having a substantially monotonic decrease in lightness value between layers from a most opaque layer underlying to a less opaque layer positioned beneath a least opaque layer, comprising:

providing a first material enclosed by a first labeled container and having a first opacity ($O_1$), and a first lightness value ($L_1$) when formed into said least opaque layer, a second material enclosed by a second labeled container having a second opacity ($O_2$) and a second lightness value ($L_2$) when formed into said less opaque layer, and a third material enclosed by a third labeled container having a third opacity ($O_3$) and a third lightness value ($L_3$) when formed into said most opaque layer, said least opaque, more opaque and most opaque layers each not being thicker than 1.5 mm, said third opacity ($O_3$) being greater than said second opacity ($O_2$), said second opacity (O2) being greater than said first opacity ($O_1$), said third lightness value ($L_3$) being greater than said second lightness value ($L_2$) and said second lightness value ($L_2$) being greater than said first lightness value ($L_1$), forming said third material into said most opaque layer on a substrate, forming said second material into less opaque layer on said most opaque layer, forming said first material into said least opaque layer on said less opaque layer.

2. The method of claim 1 wherein said third opacity ($O_3$) is 100 percent opaque.

3. The method of claim 2 wherein said second opacity ($O_2$) is from 94 percent to 99 percent opaque.

4. The method of claim 1 wherein said third lightness value ($L_3$) and said first lightness value ($L_1$) have a difference in lightness value of less than 10 Commission International de l'E'clairage (CIE) L*a*b* units.

5. The method of claim 1 further comprising hardening said first material, hardening said second material, and hardening said third material.

6. The method of claim 1 wherein said first material comprises polymerizable material, said second material comprises polymerizable material, and said third material comprises polymerizable material.

7. The method of claim 1 wherein said first material comprises a photoinitiator, said second material comprises a photoinitiator, and said third material comprises a photoinitiator.

8. The method of claim 1 wherein said first material comprises a photoinitiator and a polymerizable material said second material comprises a photoinitiator and a polymerizable material, and said third material comprises a photoinitiator and a polymerizable material.

9. The method of claim 1 wherein said first material is a liquid, paste or powder, said second material is a liquid, paste or powder, and said third material is a liquid, paste or powder.

10. The method of claim 1 wherein said first material further comprises a polymerizable material and further comprising polymerizing said polymerizable material in said first material to form first polymeric material.

11. The method of claim 1 wherein said second material further comprises a polymerizable material and further comprising polymerizing said polymerizable material in said second material to form second polymeric material.

12. The method of claim 1 wherein said third material further comprises a polymerizable material and further comprising polymerizing said polymerizable material in said third material to form third polymeric material.

13. A kit for making a dental composite, having a substantially monotonic change in lightness value between layers for a most opaque layer underlying a less opaque layer positioned beneath a least opaque layer, comprising:

a first polymerizable material, said first polymerizable material comprising a polymerizable compound, said first polymerizable material being enclosed by a first labeled container and having a first opacity ($O_1$), and a first lightness value ($L_1$) when formed into said least opaque layer, a second material enclosed by a second labeled container having a second opacity ($O_2$) and a second lightness value ($L_2$) when formed into said less opaque layer, and a third material enclosed by a third labeled container having a third opacity ($O_3$) and a third lightness value ($L_3$) when formed into said most opaque layer, said least opaque, more opaque and most opaque layers each not being thicker than 1.5 mm, said third opacity ($O_3$) being greater than said second opacity ($O_2$), said second opacity ($O_2$) being greater than said first opacity ($O_1$), said third lightness value ($L_3$) being greater than said second lightness value ($L_2$) and said second lightness value ($L_2$) being greater than said first lightness value ($L_1$).

14. The kit of claim 13 wherein said second material is a polymerizable material having at least one polymerizable compound and said third material is a polymerizable material having at least one polymerizable compound.

15. The kit of claim 13 wherein said first material is a polymerizable paste having at least one polymerizable compound, said second material is a polymerizable paste having at least one polymerizable compound and said third material is a polymerizable paste having at least one polymerizable compound.

16. The kit of claim 13 wherein said first material is a polymerizable powder having at least one polymerizable compound, said second material is a polymerizable powder having at least one polymerizable compound and said third material is a polymerizable powder having at least one polymerizable compound.

17. A method of making a dental product having substantially no change in hue from a most opaque layer to the least opaque layer and a monotonic decrease in lightness value between layers from a most opaque layer to a less opaque layer positioned beneath a least opaque layer, the most opaque layer underlying the less opaque layer comprising:

provinding a first material enclosed by a first labeled container and having a first opacity ($O_1$), and a first hue ($H_1$) when formed into said least opaque layer, a second material enclosed by a second labeled container having a second opacity ($O_2$) and a second hue ($H_2$) when formed into said less opaque layer, and a third material enclosed by a third labeled container having a third opacity ($O_3$) and a third hue ($H_3$) when formed into said most opaque layer, said least opaque, more opaque and most opaque layers each not being thicker than 1.5 mm, said third opacity ($O_3$) being greater than said second opacity ($O_2$) said second opacity ($O_2$) being greater than said first opacity ($O_1$), said third hue ($H_3$) being greater than said second hue ($H_2$) and said second hue ($H_2$) being greater than said first hue ($H_1$), forming said third material into said most opaque layer on a substrate, forming said second material into said less opaque layer on said most opaque layer, forming said first material into said least opaque layer on said less opaque layer.

18. The method of claim 17 wherein said third opacity ($O_3$) is 100 percent opaque.

19. The method of claim 18 wherein said second opacity ($O_2$) is from 94 percent to 99 percent opaque.

20. The method of claim 17 wherein said third lightness value ($L_3$) and said first lightness value ($L_1$) have a difference in lightness value of less than 10 Commission International de l'E'clairage (CIE) L*a*b* units.

21. The method of claim 17 further comprising hardening said first material, said second material, and said third material.

22. The method of claim 17 wherein said first material comprises polymerizable material, said second material comprises polymerizable material, and said third material comprises polymerizable material.

23. The method of claim 17 wherein said first material comprises a photoinitiator, said second material comprises a photoinitiator, and said third material comprises a photoinitiator.

24. The method of claim 17 wherein said first material comprises a photoinitiator and a polymerizable material, said second material comprises a photoinitiator and a polymerizable material, and said third material comprises a photoinitiator and a polymerizable material.

25. The method of claim 17 wherein said first material is a liquid, paste or powder, said second material is a liquid, paste or powder, and said third material is a liquid, paste or powder.

26. The method of claim 17 wherein said first material further comprises a first polymerizable material and polymerizing said first polymerizable material in said first material to form first polymeric material, said second material further comprises a second polymerizable material and polymerizing said second polymerizable material in said second material to form second polymeric material, and said third material further comprises a third polymerizable material and polymerizing said third polymerizable material in said third material to form third polymeric material.

* * * * *